US011271413B2

(12) United States Patent
Nguyen et al.

(10) Patent No.: US 11,271,413 B2
(45) Date of Patent: Mar. 8, 2022

(54) SYSTEMS AND METHODS FOR DISINFECTING A REMOTE CONTROL USING ULTRAVIOLET LIGHT

(71) Applicant: DISH Technologies L.L.C., Englewood, CO (US)

(72) Inventors: Phuc H. Nguyen, Parker, CO (US); Christopher William Bruhn, Aurora, CO (US)

(73) Assignee: DISH TECHNOLOGIES L.L.C., Englewood, CO (US)

(*) Notice: Subject to any disclaimer, the term of this patent is extended or adjusted under 35 U.S.C. 154(b) by 75 days.

(21) Appl. No.: 16/695,965

(22) Filed: Nov. 26, 2019

(65) Prior Publication Data

US 2020/0093946 A1 Mar. 26, 2020

Related U.S. Application Data

(62) Division of application No. 15/609,682, filed on May 31, 2017, now Pat. No. 10,507,255, which is a division of application No. 14/542,283, filed on Nov. 14, 2014, now Pat. No. 9,687,576.

(51) Int. Cl.
| | |
|---|---|
| *A61L 2/10* | (2006.01) |
| *G06F 1/3231* | (2019.01) |
| *H04N 21/422* | (2011.01) |
| *H02J 7/00* | (2006.01) |
| *H02J 7/02* | (2016.01) |
| *H02J 50/10* | (2016.01) |
| *H05B 45/18* | (2020.01) |

(52) U.S. Cl.
CPC .............. *H02J 7/0042* (2013.01); *A61L 2/10* (2013.01); *G06F 1/3231* (2013.01); *H02J 7/025* (2013.01); *H02J 50/10* (2016.02); *H04N 21/42222* (2013.01); *H04N 21/42224* (2013.01); *H05B 45/18* (2020.01)

(58) Field of Classification Search
CPC .... A61L 2/10; G06F 1/3231; H04N 21/42222
See application file for complete search history.

(56) References Cited

U.S. PATENT DOCUMENTS

| | | | |
|---|---|---|---|
| 5,813,057 | A | 9/1998 | Descent et al. |
| 6,076,197 | A | 6/2000 | Yeung |
| 6,346,891 | B1 | 2/2002 | Feinleib et al. |
| (Continued) | | | |

FOREIGN PATENT DOCUMENTS

| | | | | |
|---|---|---|---|---|
| CN | 202777153 U | 3/2013 | | |
| CN | 203300019 U | 11/2013 | | |
| WO | WO-2013108229 A2 | * | 7/2013 | ........... H05B 47/115 |

*Primary Examiner* — Kevin Joyner
(74) *Attorney, Agent, or Firm* — Seed Intellectual Property Law Group LLP

(57) ABSTRACT

A remote control having an ultraviolet light emitting device for disinfecting the outer surfaces of the remote control is disclosed. In particular, the remote control may include an ultraviolet transmissive housing and internal ultraviolet emitting light emitting diodes. The ultraviolet transmissive housing allows the light from the internally mounted ultraviolet emitters to pass through the remote control's housing and kill bacteria, viruses, and other micro-organisms on the outer surface of the remote control by employing methods to automate safe and effective operations of ultraviolet light.

20 Claims, 5 Drawing Sheets

(56) References Cited

U.S. PATENT DOCUMENTS

| | | |
|---|---|---|
| 6,458,331 B1 | 10/2002 | Roberts |
| 6,490,351 B1 | 12/2002 | Roberts |
| 6,650,322 B2 | 11/2003 | Dai et al. |
| 6,720,950 B2 | 4/2004 | Cheng |
| 7,227,534 B2 | 6/2007 | Lin et al. |
| 7,889,175 B2 | 2/2011 | Kryze et al. |
| 8,084,752 B2 | 12/2011 | Ranta et al. |
| 8,203,124 B2 | 6/2012 | Havens et al. |
| 8,481,970 B2 | 7/2013 | Cooper et al. |
| 8,780,278 B2 | 7/2014 | Gulati |
| 2008/0163301 A1 | 7/2008 | Park et al. |
| 2011/0006887 A1 | 1/2011 | Shaull et al. |
| 2011/0043475 A1 | 2/2011 | Rigazio et al. |
| 2012/0074334 A1 | 3/2012 | Milligan |
| 2013/0234838 A1 | 9/2013 | Hsu |
| 2014/0131595 A1 | 5/2014 | Nathan |
| 2014/0239817 A1 | 8/2014 | Leinen et al. |
| 2015/0090903 A1* | 4/2015 | Cole .................. A61L 2/10 250/492.1 |
| 2015/0168595 A1 | 6/2015 | Nakamikawa |

* cited by examiner

SYSTEMS AND METHODS FOR DISINFECTING A REMOTE CONTROL USING ULTRAVIOLET LIGHT

BACKGROUND

Technical Field

The present disclosure generally relates to using ultraviolet light to disinfect a remote control and methods for safely and effectively using ultraviolet light.

Description of the Related Art

Ultraviolet, or UV, light is used to kill bacteria, viruses, and other micro-organisms. Exposure to ultraviolet light can harm people, but available devices and methods of using ultraviolet light to kill bacteria, viruses, and other micro-organisms rely on active human interaction. For example, ultraviolet disinfecting wands are activated by an operator and held or waved over the object the operator seeks to disinfect. The wands may be shielded to protect the user and, in particular, the user's eyes, from the ultraviolet light, but still require a user to hold the wand and be present to carry out the disinfecting process. Some disinfecting apparatuses fully enclose the object the operator seeks to disinfect and completely contain the ultraviolet light used to disinfect the object, but such apparatuses require a person to take active steps to place the object in the apparatus.

BRIEF SUMMARY

One or more embodiments disclosed herein are directed to a remote control having an ultraviolet light emitting device for disinfecting the outer surfaces of the remote control. In particular, the remote control may include an ultraviolet transmissive housing and internal ultraviolet light emitters. The ultraviolet transmissive housing allows the light from the internally mounted ultraviolet light emitters to pass through the remote control's housing and kill the bacteria, viruses, and other micro-organisms on the outer surface of the remote control.

In one embodiment, the remote control may also implement a method for determining whether it is safe to activate the ultraviolet light. For example, the remote control may include or be networked to a variety of sensors and devices to aid in determining when or if a user is likely to be in the same room or otherwise near the remote control. The remote control may use a microphone to listen for voices, a light sensor to detect the lights in the room or the fluctuations of light coming from a television, motion sensors to determine whether someone is holding the remote control, or wireless or radiofrequency communication to communicate with other devices to determine whether a person is near the remote control.

In one embodiment, the remote control may communicate with a set-top box, such as a satellite receiver, digital video recorder, or cable receiver to determine whether a person is near the remote control. The set-top box may include sensors and devices to aid in determining when or if a user is likely to be in the same room or otherwise near the remote control. The set-top box may include a connection to an attached television and be able to determine whether the television is on based on the status of that connection. The set-top box may also include or be networked to a camera or motion sensor to determine whether a person is in the room with the set-top box.

In one embodiment, a remote control charging pad may include an inductive coil for transferring energy to the remote control for recharging the remote control. The remote control charging pad may also include sensors for determining whether a user is near the remote control, for determining the location and orientation of the remote control on the charging pad, or for communicating with the remote control or a set-top box to aid in determining whether a person is near the remote control and when to activate the charging pad ultraviolet light emitters to disinfect the remote control.

In one embodiment, a method for determining when to activate ultraviolet light emitters is disclosed. The method may include a remote control receiving information from one or more sensors or devices associated with a set-top box, a remote control, a smartphone, a home security system, a home automation system, or other devices. The remote control may determine whether a user is likely to be away from the remote control based on the received information and may activate ultraviolet light emitters if the user is determined to be away from the remote control.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements are not necessarily drawn to scale, and some of these elements may be enlarged and positioned to improve drawing legibility and understanding of the features.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with devices, remote controls, charging devices, and set-top boxes have not been shown or described in detail to avoid unnecessarily obscuring descriptions of the embodiments.

Unless the context requires otherwise, throughout the specification and claims that follow, the word "comprise" and variations thereof, such as "comprises" and "comprising," are to be construed in an open, inclusive sense, that is, as "including, but not limited to."

References throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment.

The use of ordinals such as first, second and third does not necessarily imply a ranked sense of order, but rather may only distinguish between multiple instances of an act or structure.

The headings and Abstract of the Disclosure provided herein are for convenience only and do not limit the scope or meaning of the embodiments.

Figure 1:
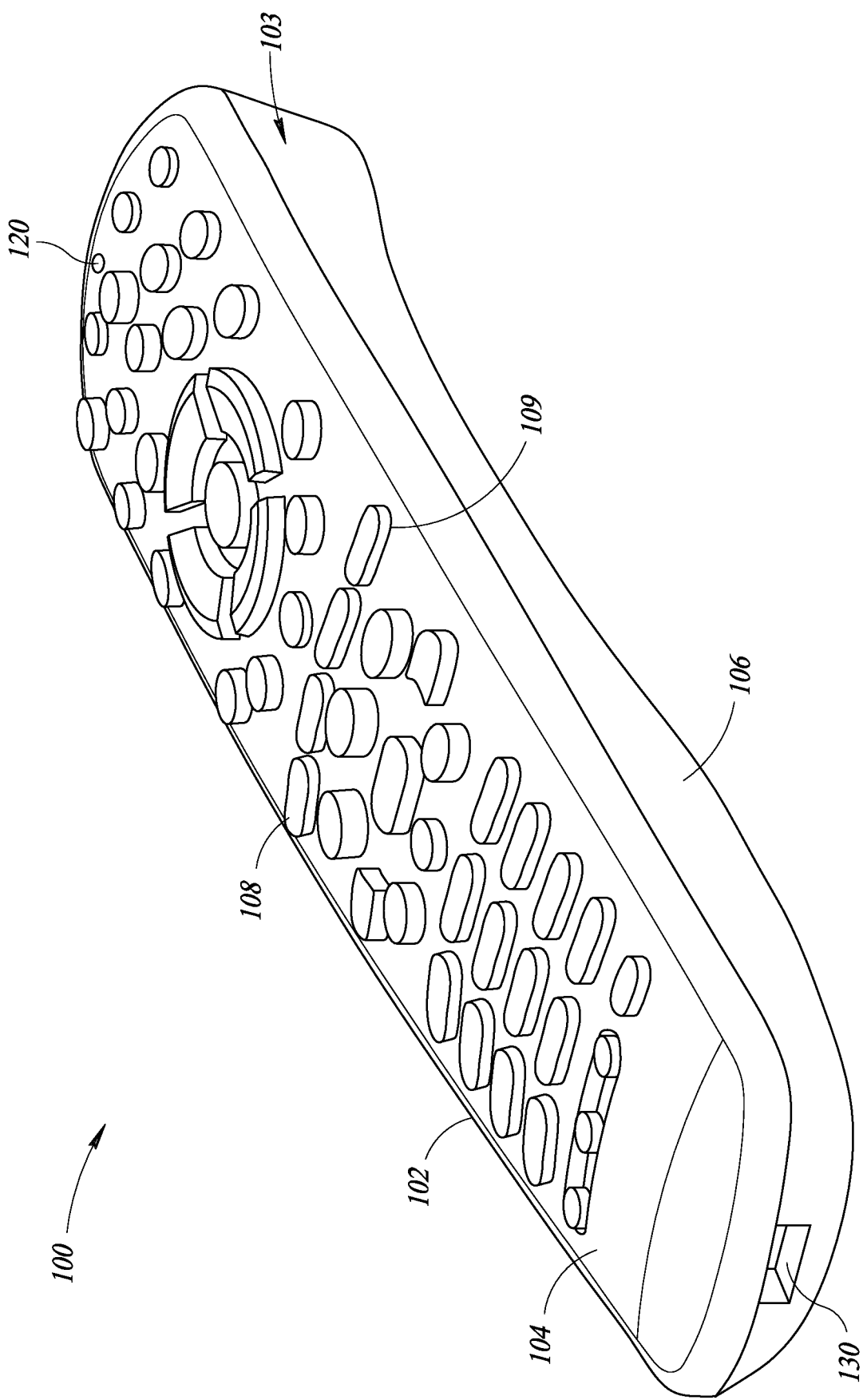
FIG. 1 is a isometric view of a remote control according to one embodiment of the present disclosure.

FIG. 1 is a diagram of a remote control 100. In one embodiment, the remote control 100 is a self-disinfecting remote control. The remote control 100 includes a housing 102. The housing 102 includes an outer surface 103, a top portion 104, and bottom portion 106. The top portion 104 may be coupled to the bottom portion 106. Each of the top portion 104 and bottom portion 106 may include side portions. The top portion 104 may include apertures 109 through which control buttons 108 may protrude. When using the remote control 100, a person may hold or grip the housing 102 and issue commands to other devices, such as a television 600, see FIG. 5, by pressing or otherwise interacting with the buttons 108.

Remote controls are often communal devices. For example, during any given day the remote control 100 may be used to control a family television by a parent in the morning to watch the weather report, a child in the afternoon after school, the parents again to watch the evening news and a football game, and even non-family members such as a visiting friend or a babysitter. Each person using the device may transfer germs, viruses, bacteria, and other microbes from their hands to the remote control. Remote controls are also often used during or just after a possible high-germ activity, for example, while eating food, just after coming in from outside, coughing into the person's hands, or the like. Further the remotes are often left on the floor where people have walked or dropped items, or family pets might get ahold of them. Various germs, including viruses, bacteria, and other microbes are deposited on the outer surface 103 and buttons 108 of the remote control 100. A further problem is that the germs might enter cracks in the housing, such as below a button or at the edge of the battery case, down where conventional cleaning will not remove them.

Figure 2:
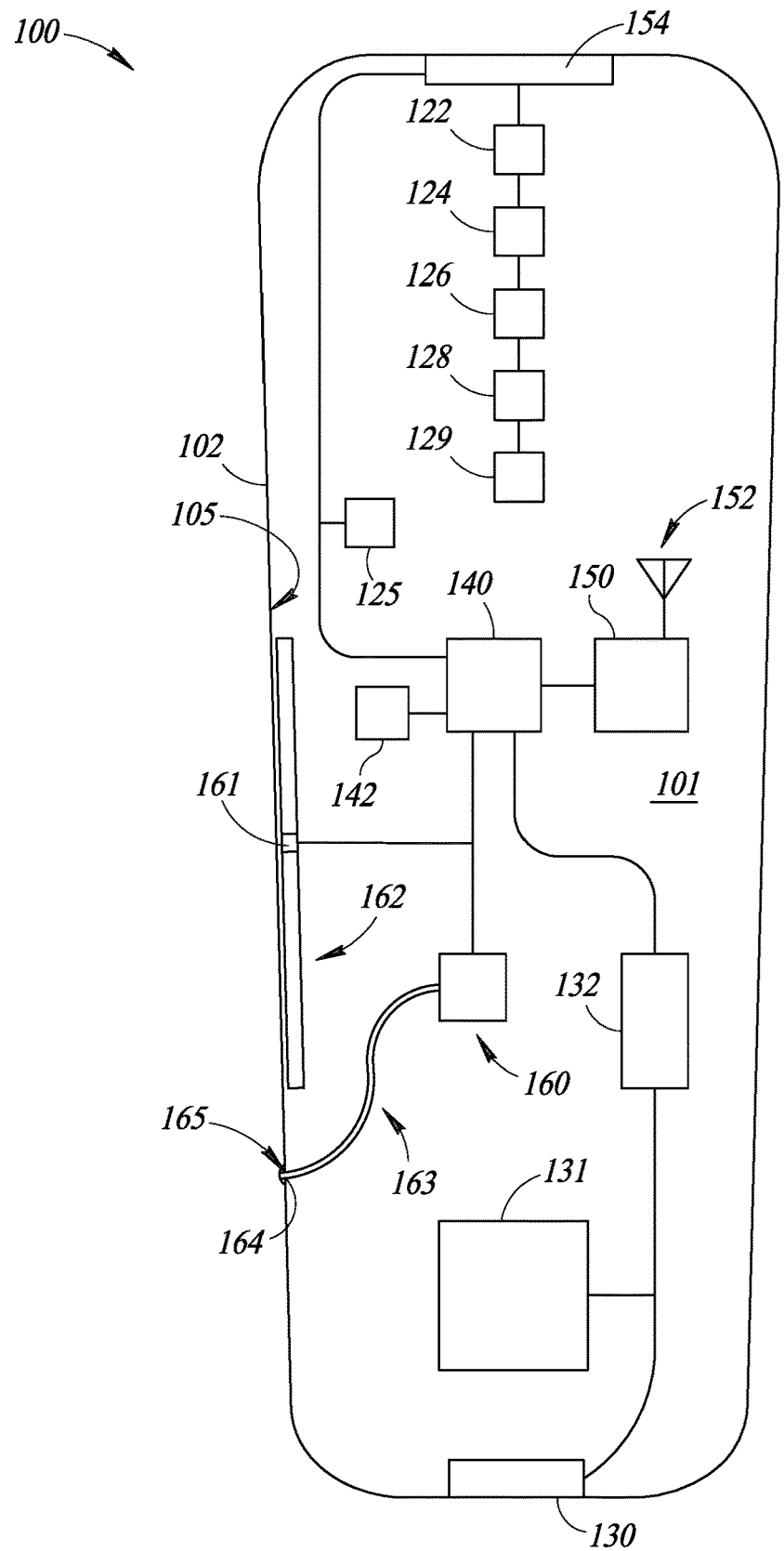
FIG. 2 is a diagram of the internal components of the remote control of FIG. 1 according to one embodiment of the present disclosure.

Referring to FIGS. 1 and 2, to kill contaminants, such as germs, viruses, bacteria, and other microbes, the remote control 100 includes within the housing 102 ultraviolet light emitters 142, 160, 161 that, when activated, emit ultraviolet light that can kill the contaminants. The remote control 100 may include one or more ultraviolet light emitters of one or more different types.

The remote control 100 may include a light emitting diode (LED) ultraviolet light emitter 142. When activated, the LED ultraviolet light emitter 142 emits ultraviolet light that disinfects the outer surface 103 of the remote control 100. In one embodiment, the LED ultraviolet light emitter 142 is mounted in the inner cavity 101 of the remote control 100 and emits light outward towards the housing 102 of the remote control 100. The typical polymer material used in making the housing of a remote control and its buttons absorbs a significant portion, if not all, of the ultraviolet light strikes its surface. Therefore, in embodiments wherein the LED ultraviolet light emitter 142 emits light from the inner cavity 101 out towards the housing 102 and outer surface 103 of the remote control 100, the housing 102 includes ultraviolet transmissive material. The ultraviolet transmissive material used in manufacturing the housing 102 may not transmit 100% of the ultraviolet light emitted by the LED ultraviolet light emitter 142. The ultraviolet transmissive material from which the housing 102 is made should transmit enough UV light, taking into account, for example, the thickness of the housing 102, and the amount of ultraviolet light emitted by the LED ultraviolet light emitter 142, that the outer surface 103 of the remote control 100 receives sufficient ultraviolet light to kill or render inert the contaminants on the outer surface 103 of the remote control 100. Similarly, the material used to make the buttons 108 may also be made from ultraviolet transmissive material.

In some embodiments, the remote control 100 may include an ultraviolet light emitter 160 coupled to one or more light pipes 163. The light pipes 163 may be a type of fiber optic material that receives ultraviolet light from the ultraviolet light emitter 160 and directs it out to the outer surface 103 of the remote control 100. In some embodiments, the light pipes 163 may transmit ultraviolet light to or through apertures in the housing 102, such as aperture 164 and button apertures 109. In some embodiments, the ends of the light pipes 163 may direct the ultraviolet light from the ultraviolet light emitter 160 onto the outer surface 103 of the remote control 100; for example, the light pipes 163 may protrude up through the button apertures 109 and then bend and direct the ultraviolet light back onto outer surface 103. In some embodiments, the end of the light pipes 163 may direct ultraviolet light into a lens or other device, such as a lens 165 that further directs the ultraviolet light onto the outer surface 103 of the remote control 100.

In some embodiments, the remote control 100 may include an ultraviolet light emitting LED 161 configured to direct light into light guide 162. In some embodiments, the ultraviolet light emitting LED 161 may be coupled, affixed, or integrated with the light guide 162. In its most basic form, the edge of a light guide, such as light guide 162, receives light from a light source and then distributes the light over a surface. Some light guides use a combination of total internal refraction and imperfections within the light guide to distribute light over a area. The total internal refraction properties of the light guide aid in keeping the light within the light guide while the imperfections, such as surface ridges or grooves, act to change the direction of the light and cause the light to leave the light guide and illuminate a surface.

The light guide 162 receives ultraviolet light at its center from the ultraviolet light emitting LED 161 and distributes the light along an inner surface 105 of the housing 102 and also internal to the walls of the housing 102. The housing 102, being made from ultraviolet transmissive material, can transmit the ultraviolet light though the housing 102 and to the outer surface 103, where it can kill containments.

Although depicted as a separate structure in FIG. 2, in some embodiments, the light guide 162 can be integrated into the housing 102. In some embodiments, the housing 102 itself may be a light guide. In such embodiments, the housing 102 may receive light from an ultraviolet light emitter, such as ultraviolet light emitting LED 161, and distribute the light though the housing 102 to the outer surface 103.

As discussed above, the remote control 100 may include sensors, devices, and other means for determining the presence or absence of people near the remote control 100.

The remote control 100 may include one or more light sensors 122. The light sensor 122 may be positioned within the inner cavity 101 of the remote control 100 and beneath a window 120 that transmits light from outside the remote control 100 to the light sensor 122. The light sensor 122 is coupled to a controller 140. The light sensor 122 can transmit information related to the light in the environment surrounding the remote control 100.

In some embodiments, the light sensor 122 may be located on the outer surface 103 of the remote control 100 or otherwise located where it may receive or evaluate all possible light in the environment surrounding the remote control 100. In addition, the remote control 100 may include light sensors 122 in more than one location in the remote control 100. The remote control 100 may include light sensors 122 located and configured to measure light falling on one or more locations of the top portion 104, the bottom portion 106, or other areas of the remote control 100.

The controller 140 receives information from the light sensor 122 and may use that information in determining whether a person is near the remote control 100. For example, a brightly lit room may indicate that a person is present in the room with the lights on. Therefore, the controller 140 may determine that the level or amount of light in the room may indicate that a person is present. In some embodiments, the amount of light received in the light sensor may be low, yet a person may still be present in the room. The light sensor 120 might be sensitive to whether the light being sensed is from a fluorescent source, an incandescent source, an LED, or an OLED display, such as the TV itself. Also, a person may turn the lights on and off, indicating that a human is near the remote. For example, a person may watch television in a relatively dark room, but the light from the television may cause fluctuations in the amount of light in the room. In such a situation, the controller 140 may evaluate the change in light level readings from the light sensor 122 over time and determine whether a person is present in the room based on overall light levels that fluctuate over time.

The remote control 100 can include one or more sound sensors, such as a microphone 124. The microphone 124 may be positioned within the inner cavity 101 of the remote control 100 and, for example, positioned beneath an aperture in the housing 102 of the remote control 100 such as the button apertures 109. The microphone 124 is coupled to the controller 140 and may transmit information related to the sound in the environment surrounding the remote control 100.

The microphone 124 measures the sound pressure levels in the environment surrounding the remote control 100, and the controller 140 receives information from the microphone 124 and may use that information in determining whether a person is near the remote control 100. For example, a loud room with high fluctuations in sound pressure levels may indicate that a person is present in the room. Therefore, the controller 140 may determine that the level or amount of sound in the room indicates that a person is present. In some embodiments, the sound in the environment surrounding the remote control may not be constant or high, yet a person may still be present in the room. For example, a person may be sitting on a couch or lying in bed reading and may only make quiet noises every few minutes. In such a situation, the controller 140 may monitor the sound levels over a period of time, for example, over two, five, ten, or fifteen minutes, and, based on the sound levels over time, determine that a person is present in the room.

The remote control 100 can include one or more temperature sensors, such as temperature sensor 126, which may be a thermometer. The temperature sensor 126 may be positioned within the inner cavity 101 of the remote control 100. The temperature sensor 126 may be positioned beneath an aperture in the housing 102 of the remote control 100, for example, the temperature sensor 126 maybe located beneath the button apertures 109 or near another aperture that facilitates measuring the temperature of the environment near the remote control 100. In some embodiments, the temperature sensor 126 may be located on the outer surface 103 of the remote control 100 or integrated into the housing 102 of the remote control 100.

The temperature sensor 126 is coupled to the controller 140. The temperature sensor 126 transmits information related to the temperature of the remote control 100 or the environment surrounding the remote control 100. The controller 140 receives information from the temperature sensor 126 and may use that information in determining whether a person is near or holding the remote control 100. The controller 140 may determine that a person is holding the remote control 100 based on the temperature of a surface mounted temperature sensor 126. For example, a surface mounted temperature sensor 126 may indicate a temperature above a predetermined threshold, such as above 80 degrees Fahrenheit, and the controller 140 may determine a user is present when the temperature from the temperature sensor 126 exceeds an 80 degree Fahrenheit threshold. The temperature sensor also monitors for fluctuations in temperatures. If the temperature changes a few times each hour, as may happen if a person is holding the device, or the HVAC of the home is active in the room in which the remote is located, then this indicates a high likelihood a person is present. But if there are no changes in temperature for a few hours at a time, this indicates that no person is likely present.

In some embodiments, a high or low temperature may be indicate that a user is not near the remote control 100. For example, during cold weather months many people turn their thermostat set point down when they leave the house for work or when everyone in the house goes to bed. During such cold weather seasons the controller may determine that no person is near the remote control when the ambient temperature drops more than a predetermined amount, such as three degrees below the daily indoor high or below a 72 degree Fahrenheit threshold. As another example, during warm weather months, many people turn their thermostat set point up when they leave the house. During such warm weather seasons the controller may determine that no person is near the remote control when the temperature raises more than a predetermined amount, such as three degrees above the daily indoor low or above a 78 degrees Fahrenheit threshold.

The remote control 100 can include one or more motion sensors, such as an accelerometer 128 and a gyroscope 129. The motion sensors 128, 129 may be positioned within the inner cavity 101 of the remote control 100 or otherwise coupled to the housing of the remote control 100. The motion sensors 128, 129 may measure acceleration or angular movement in one or more axes. In some embodiments, the motion sensors 128, 129 measure acceleration or angular movement in three orthogonal axes.

The motion sensors 128, 129 are coupled to the controller 140. The motion sensors 128, 129 transmit information related to the movements of the remote control 100. The controller 140 receives information from the motion sensors 128, 129 and may use that information in determining whether a person is near the remote control 100. For example, the controller 140 may determine that a person is holding the remote control 100 based on the movement information received from the motion sensors 128, 129. If the motion sensors 128, 129 indicated that the remote control 100 is currently moving, then the controller 140 may determine that a person is near to or holding the remote control 100. As another example, the remote control 100 may be moving despite being held by a person. In such situations, by using a multi-axis accelerometer 128, the controller can receive acceleration information which may indicate the position of the remote control 100. If the position information indicates that the remote control is lying flat, for example, as it would on a table, then the controller 140 may determine that a person is likely not holding it, while if the acceleration information indicates that the remote control is at an inclined angle with respect to the acceleration due to gravity, then the controller 140 may determine that the remote control 100 is being held by a person.

In some embodiments, one of the motion sensors 128, 129 may include both an accelerometer, such as a three-axis accelerometer, and a gyroscope, such as a three-axis gyroscope. Such a configuration may be called an inertial measurement unit or IMU. The IMU may send movement and position information to the controller 140 for use in determining whether a person is near the remote control 100.

The remote control 100 may include a sonar system. The sonar system may include a transmitter, such as a sonar transmitter 125 and a receiver, such as the microphone 124. The sonar transmitter 125 may be positioned within the inner cavity 101 of the remote control 100 and behind apertures in the housing 102, on the outer surface 103 of the remote control 100, or in another location, such as on a wall of a room.

The sonar transmitter 125 is coupled to the controller 140. The sonar transmitter 125 and microphone 124 work together to determine whether a person is present. The sonar transmitter may transmit high frequency pulses or pings. These pulses bounce off of people and objects in the room or near the remote control 100 and the microphone 124 receives these echoes and, based on the properties of the echoes, the remote control 100 and controller 140 may determine whether or not a person is in the room or otherwise near the remote control 100.

The charging pads 200, 300 security system 636, set-top box 500, and other devices may include the sonar transmitter 125 and microphone 124 to aid in determine the location and presence or absence of a person. As with the other sensors and devices, additional sonar transmitters 125 and microphones 124 may help more accurately detect the location and presence or absence of a person.

The remote control 100 may include a power system. The power system may include one or more power inputs, such as power port 130 and induction charger 131. The power system may also include power storage, such as a capacitor, or a battery 132. The power system provides power to the remote control 100 and its components, for example, the controller 140; the wireless transceiver 150; the sonar transmitter 125; the sensors 122, 124, 126, 128, 129; and the ultraviolet light emitters, such as the ultraviolet light emitters 142, 160, 161.

The induction charger 131 transfers energy between a power source, such as, the charging pad 200, and the remote control 100 through an electromagnetic field. The power transferred from the power source may be used to recharge or otherwise store energy in the battery 132, or to power the other components of the remote control 100. In some embodiments, the induction charger 131 may simultaneously charge the battery 132 and provide power to the other components of the remote control 100.

Similarly, the power port 130 may supply energy to recharge or otherwise store in the battery 132, or to power the other components of the remote control 100, either simultaneously or one at a time.

The controller 140 may receive information from the charging system. The information may be as simple as receiving power to turn on the remote control 100, but may also include information such as charging status and whether the induction charger 131 or the power port 130 are receiving power from a power source. The controller 140 may use the information from the charging system to aid in determining whether a person is near the remote control 100. For example, the remote control 100 is typically used as a wireless device and freely moved around during use. Therefore, when the remote control 100 is receiving power through the power port 130, the remote control 100 is likely attached to a power adapter that is plugged into the wall and may not be in use or located near a person, and when the remote control 100 is receiving power through the induction charger 131, the remote control 100 is likely positioned on an induction charger power source and may not be in use or located near a person.

The remote control 100 may include a wireless communication system including, but not limited to, an infrared (IR) transceiver 154, one or more wireless transceivers 150, and one or more wireless antennas 152. The wireless communication system is configured to transmit and receive wireless signals. The wireless signals are generally radio signals, such as RF4CE, Bluetooth, and Wi-Fi, but can also be infrared signals or any other wireless signal.

The wireless communication system may monitor wireless communications near the remote control 100 or communicate with other devices near the remote control 100.

The remote control 100 may actively or passively monitor wireless communication traffic to aid in determining whether a user is near the remote control 100. For example, if the IR transceiver 154 is monitoring IR signals near the remote control 100 and receives an IR signal, even one not directed to the remote control 100, the IR transceiver may send information to the controller 140 that indicates that an IR signal was received. The controller 140 may use this information in determining whether a person is near the remote control 100, for example, detecting an IR signal may be indicative of a person using a second remote control in the same room as the remote control 100.

Similarly, the wireless transceiver 150 may actively or passively monitor wireless traffic, for example, based on the received Wi-Fi signal strength, such as Wi-Fi traffic on nearby wireless area networks to help determine whether a person is near the remote control 100. For example, if the wireless transceiver 150 monitors the Wi-Fi traffic and determines that an access point is nearby, for example by receiving the broadcast SSID of the access point, but there is no other network traffic going to or coming from that access point, the controller 140 may determine that it is likely that no people are in the area. For example, most people carry a smartphone with them everywhere and their smartphone may automatically connect to the access point when they are home and regularly transmit data over the Wi-Fi network to check email, social networks, and for other reasons, thus if no network traffic or low signal strength is detected, the person's smartphone, and therefore the person, are likely not near the remote control. Alternatively, if the wireless transceiver 150 detects high signal strength, then the person is in proximity of the remote control.

The remote control 100 may also communicate with other devices though the wireless communication system. In some embodiments, the remote control 100 may communicate with other devices to send commands to them, such as to turn on a television, change a channel, or record a show, and, as discussed in more detail later, may also communicate with other devices to receive information that aids in determining whether a person is near the remote control 100.

The controller 140 of the remote control 100 may include a processor, memories, input/output ports, and other components commonly used in computers or controllers. The controller 140 may also include programs for carrying out the methods and processes disclosed herein, including, but not limited to, the communication with the sensors 122, 124, 126, 128, 129, the sonar transmitter 125, the ultraviolet light emitters 142, 160, 161, power systems, and a wireless communication system, determining whether a person is near or in the same room as the remote control 100, activating or turning on the ultraviolet light emitters 142, 160, 161, and communicating with other devices, for example, set-top boxes, security systems, thermostats, smart appliances, or the like.

By way of example, the controller 140 may use a number of different sources of information to determine that a person is not likely near the remote control 100. In some embodiments, the controller 140 may receive temperature information from a surface mounted temperature sensor 126 indicating that the surface temperature of the remote control is below a threshold of 68 degrees Fahrenheit, sound pressure level information from the microphone indicating that the ambient noise in the room is below a threshold of 25 dB, light sensor information indicating that the luminous flux in the room is steady and below a threshold of 5 lux, and information over the wireless network from a set-top box indicating that the television is turned off.

Further sensors include time sensors, both time of day and time since last moved, exposed to high light, high sound, etc. In the first, time of day, the remote can obtain the time of day from its own internal clock. Alternatively, the remote can obtain the time of day by communication with the set-top box. Television is rarely watched at 2:00 a.m. or 3:00 a.m. The remote can therefore use this as one factor to determine that a person is not present.

In addition to tracking the time of day, the remote can also store a history of the time of day in which is has been used for the last several months. Generally, use in a household follows a predictable pattern with respect to a time of day. For example, young children may watch television for a few moments each morning before going to school or the parents may check the weather before the start of the day. Then, the television remote may remain idle for several hours, even to the lunch hour, or until children return from school or the parents return from work. After a period of several days or weeks, the remote can store a history of the time of day when it is not used, and can use the time of day, as well as the history of no use for several weeks during a particular time of day, as a further data point that a person is not likely adjacent to the remote.

When determining whether the remote has been used at a particular time of day, the most reliable indication will be whether a button on the remote has been pressed within a certain time period. For example, when a remote is first used, a button is pressed to turn on the television, and in addition, the volume will likely be adjusted. When the remote is no longer going to be used, the OFF button will be used to turn the television off. These are steps which can be measured and stored in the controller 140 as an indication that a person was present during that time period, since it can be assumed that only a person would use the remote to turn the television on and off or change the volume. Accordingly, the times of day in which no button has been pressed for long periods of time can be stored in the controller 140, and this can be used as a data point for an indication that a user was not present during that time. If each day has large blocks of time during which the remote has not been used, for example during the midday or at nighttime between the hours of 1:00 a.m. and 4:00 a.m., after collecting the data for several weeks, this can provide an indication that the likelihood of use during these time periods is extremely low. On the other hand, in some households, the viewing habits may be to watch TV between 2:00 a.m. and 4:00 a.m., for example if the homeowners work an odd shift, or some other reason. Accordingly, by accumulating a use history and learning a time of day when the remote is not in use for several hours at a time, which extends for several weeks or months, the controller 140 can use this as a data point, either alone or in combination with the other data as described herein to determine that no person is present, and thus perform the UV cleaning during these time periods.

In addition to a time of day sensor and data point, the controller 140 may include a timer for each of the other sensors or devices which have been described herein. For example, the time since the accelerometer 128 or the gyroscope 129 have been activated can be determined, and after a long time has passed with no activation, this is another data point to indicate that a person is not likely adjacent to the remote. Similarly, the changes over time from the other sensors, such as temperature changes, sound changes, and other changes over time can be monitored, and when one of the sensors indicates no change for long periods of time, this can be other data points that a person is not likely present. Thus, not only is low noise or low light one of the indications that a person is not present, but the time which has passed since the noise changed or the light changed, or the time over which the light level and noise level has been maintained below a certain value, are also data points which can be used to determine that a person is likely not present.

Based on this information, the remote control may determine that all the sensors and devices have each sent information to the controller 140 that indicates that a person is not near the remote control 100. For example, a surface temperature of 68 degrees may indicate that the remote control 100 is not being held, the 25 dB sound level indicates that no person is in talking or moving around near the remote control 100, the light level below 5 lux indicates that the lights in the room are off and no television is on, and the set-top box provides corresponding information that the television is off. Based on this data the remote may determine that no person is near the remote control 100 and it may be safe to activate the ultraviolet emitters 142, 160, 161 to disinfect the remote control 100. In some embodiments, less than all of the information may indicate that no people are in the room and the controller 140 may still activate the ultraviolet light emitters 142, 160, 161.

Cleaning and disinfecting the remote control 100 with ultraviolet light can take a few seconds to several minutes. Before activating the ultraviolet lights, the remote control 100 may determine, for example, based on past experience, the likelihood that a person will enter the room during the cleaning. For example, if the remote control 100 determines that no person is present in the room at 7:55 PM, but knows the cleaning cycle takes five minutes, and a user typically enters the room just before 8:00 PM to start watching a television show, the remote control 100 may not activate the ultraviolet emitters because it may not be able to finish the cleaning cycle before a person enters the room. In some embodiments, the remote control 100 may initiate a shorter cleaning cycle when it expects a person to enter a room before completion of a full cleaning cycle.

If the remote control 100 activates the ultraviolet emitters to start a cleaning cycle, but then detects a person entering the room, then the remote control 100 may immediately deactivate the ultraviolet emitters to prevent accidental exposure to the person that entered the room.

In addition, the remote control 100 may use sensors to determine whether a user has a cold or infection. For example, the remote control 100 may use the microphone 124 to detect coughing, sneezing, or sniffling, the temperature sensors 126 to detect an elevated temperature of the user holding the remote control 100, or the cameras 523, 623 to look for visual indications that a user is sick.

In some embodiments, the set-top box 500 may use facial recognition to find and recognize faces in images from the camera 523 in the set-top box 500. The set-top box 500 may also analyze the color tone of a person's skin to aid in determining whether a person is sick or not. For example, a paler than normal skin tone or a more red then normal nose may indicate that the person has a cold or is sick.

If the remote control 100 determines that a user is sick the remote control 100 may prioritize cleaning. For example, if the remote control 100 determines that a sick user has ceased using the remote control 100 and left the room, the remote control 100 may activate the ultraviolet emitters to start disinfecting the remote control 100, even when the remote control 100 does not expect to have a long time window during which to clean the remote control 100.

If a sick user stops using the remote control 100 or leaves the room and another user is detected in the room or using the remote control 100, the remote control 100 may prompt the healthy user to allow the remote control 100 to active the ultraviolet emitters to clean the remote control 100. For example, the remote control 100 may interact with the set-top box 500 or television 600 to display a message to the user and confirm the cleaning. In some embodiments, the healthy user may authorize the cleaning and insert the remote control 100 into an enclosed charging pad, such as the enclosed charging pad 300, or the user may leave the room for several minutes during the cleaning.

In some embodiments, the remote control 100 may be cleaned on a regular cycle, such as once a week, every two or three days, or more often, depending on how the remote control 100 is used. For example, when the remote control 100 is used by only one healthy person, the remote control 100 may be cleaned once a week, but when used by a large group of people the remote control 100 may be cleaned once a day, or even more often.

The remote control 100 may also monitor or record the parts of the remote control 100 that a user interacts with and may record this information or may transmit this information to the set-top box 500. For example, the remote control 100 may record that a user may only interacts with the number buttons or the pause and play buttons or mainly holds a certain portion of the housing of the remote control 100. In some embodiments, only ultraviolet light emitters associated with the parts of the remote control 100 that the user has interacted with or has interacted with the most are activated during cleaning. By only activating certain ultraviolet light emitters, less energy is used and batter power is conserved.

Figure 3:
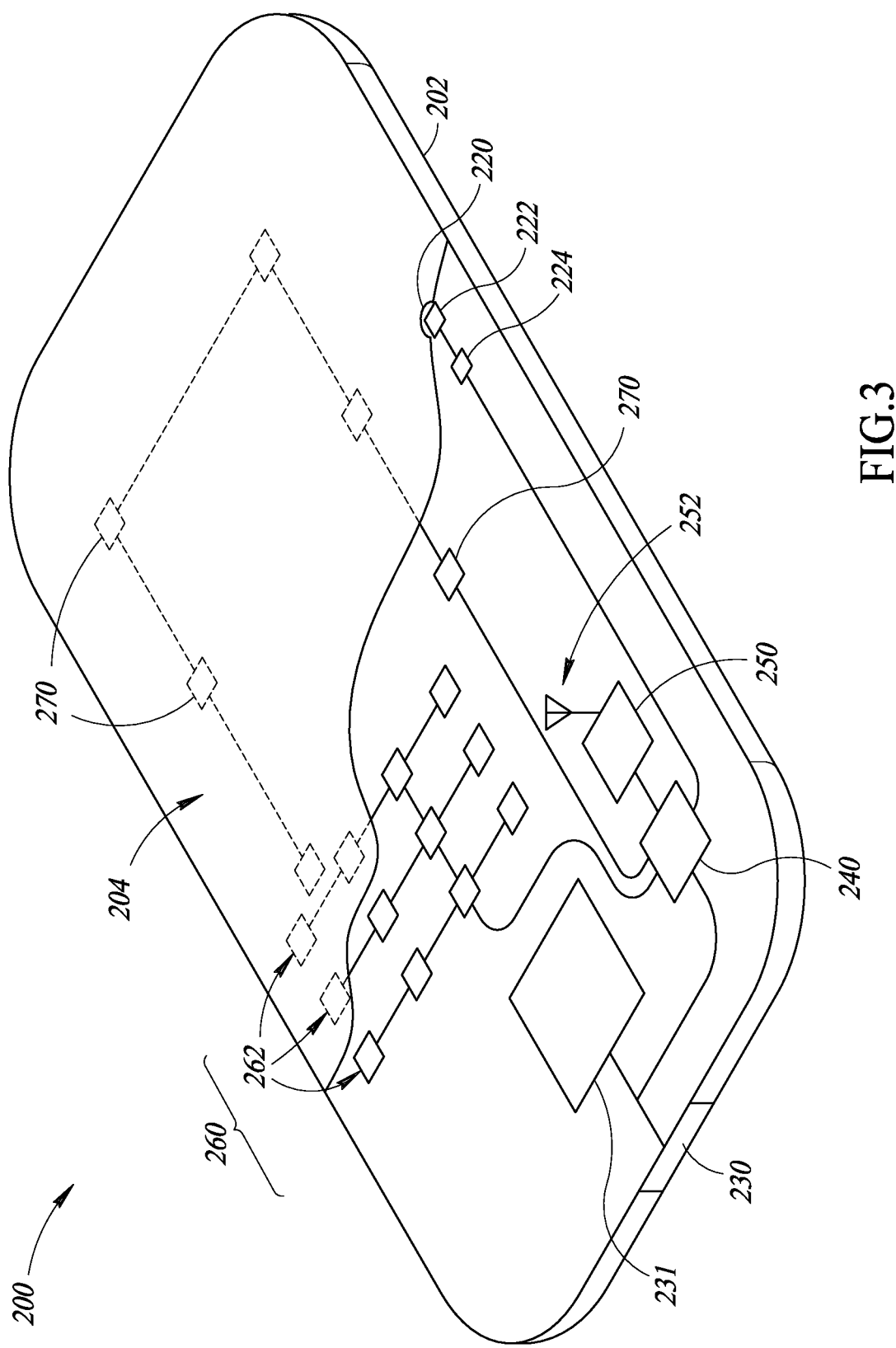
FIG. 3 is a partial cutaway view of a charging pad according to one embodiment of the present disclosure.

Referring to FIG. 3, an embodiment of a charging pad 200 in partial cutaway is shown. The charging pad 200 includes a housing 202 and a top surface 204. The top surface 204 is configured to receive a handheld device, such as a remote control (e.g., remote control 100), for example by placing the remote control 100 on top of the top surface 204.

The charging pad 200 includes sensors 222, 224 coupled to a controller 240. The light sensor 222 may have a structure and functionality similar to the light sensor 122 discussed above with reference to the remote control 100 in FIG. 1, for example, the light sensor 222 may be located beneath a window 220. Likewise, the microphone 224, the controller 240, and the wireless system, including wireless transceiver 250 and antenna 252, may also have a similar structure and functionality as the systems and parts discussed above with respect to the remote control in FIG. 1.

The charging pad 200 may include a charging system. The charging system can include an inductive charger 231 and a power port 230. The power port receives energy from outside the charging pad 200 and provides it to the rest of the charging pad 200. The inductive charger 231 receives energy from the power port 230 and provides the energy to the remote control 100 through an electromagnetic field.

The charging pad may also include one or more proximity sensors, for example proximity sensors 270. The proximity sensors 270 are arranged in a two dimensional array such that they may aid in determining the location and orientation of the remote control 100 when it is placed on the charging pad 200. For example, the controller 240 may receive proximity information from the each of the proximity sensors 270 and may determine the location and orientation of remote control 100 on the charging pad 200 based on that information. Although depicted as having six proximity sensors 270, the charging pad 200 may include more or less proximity sensors 270.

The charging pad also includes the controller 240 that may send or receive information from the remote control 100 or other device, such as a set-top box, to aid in determining whether a person is likely near the charging pad 200 or remote control 100. In some embodiments, the charging pad 200 may send information to the remote control 100 which the remote control 100 then uses in determining whether or not to active the ultraviolet light emitters 142, 160, 161. In some embodiments, the charging pad 200 receives information from the remote control 100 to determine whether a person is near the charging pad 200 and whether to activate the ultraviolet emitters 262.

The ultraviolet emitters 262 are arranged in an ultraviolet emitter array 260 and the controller 240 may control the activation of the ultraviolet emitters 262 in the array 260. The array 260 can include ultraviolet LEDs distributed along the length and width of the top surface 204 of the charging pad 200. In some embodiments, the LEDs may be coupled to the top surface 204. In some embodiments, the top surface 204 may be made from ultraviolet light transmissive material and the LEDs may be positioned below the top surface 204 and within the housing 202. The controller 240 activates the ultraviolet emitters in the array 260 when the controller 240 determines that a remote control 100 is placed on the charging pad 200 and that a person is likely not near the charging pad 200. Although depicted as having an array of ultraviolet emitters 262 in FIG. 3, in addition to or in place of the ultraviolet emitters 262, the charging pad 200 may use light pipes or light guides to distribute the ultraviolet light and disinfect the surface of a remote control 100.

Each of the ultraviolet emitters 262 may be associated with one or more proximity sensors 270, in particular, the ultraviolet light emitters 262 may be associated with a nearest one or more of the proximity sensors 270. In some embodiments, when the controller 240 activates the ultraviolet light emitters 262, the controller 240 only activates the ultraviolet light emitters 262 associated with proximity sensors 270 that indicate they are near an object, such as the remote control 100.

In some embodiments, the charging pad 200 may determine the location and orientation of the remote control 100 on the charging pad 200 and may activate the ultraviolet emitters 262 in close proximity to the remote control 100 or directly beneath the remote control 100. In this way, the charging pad 200 may conserve energy and reduce the amount of stray ultraviolet light.

In some embodiments, the charging pad 200 may receive information or commands from another device, such as the remote control 100 or a set-top box, that indicate that no people are near the charging pad 200. Based on this information, the charging pad 200 will activate the ultraviolet emitters.

Figure 4:
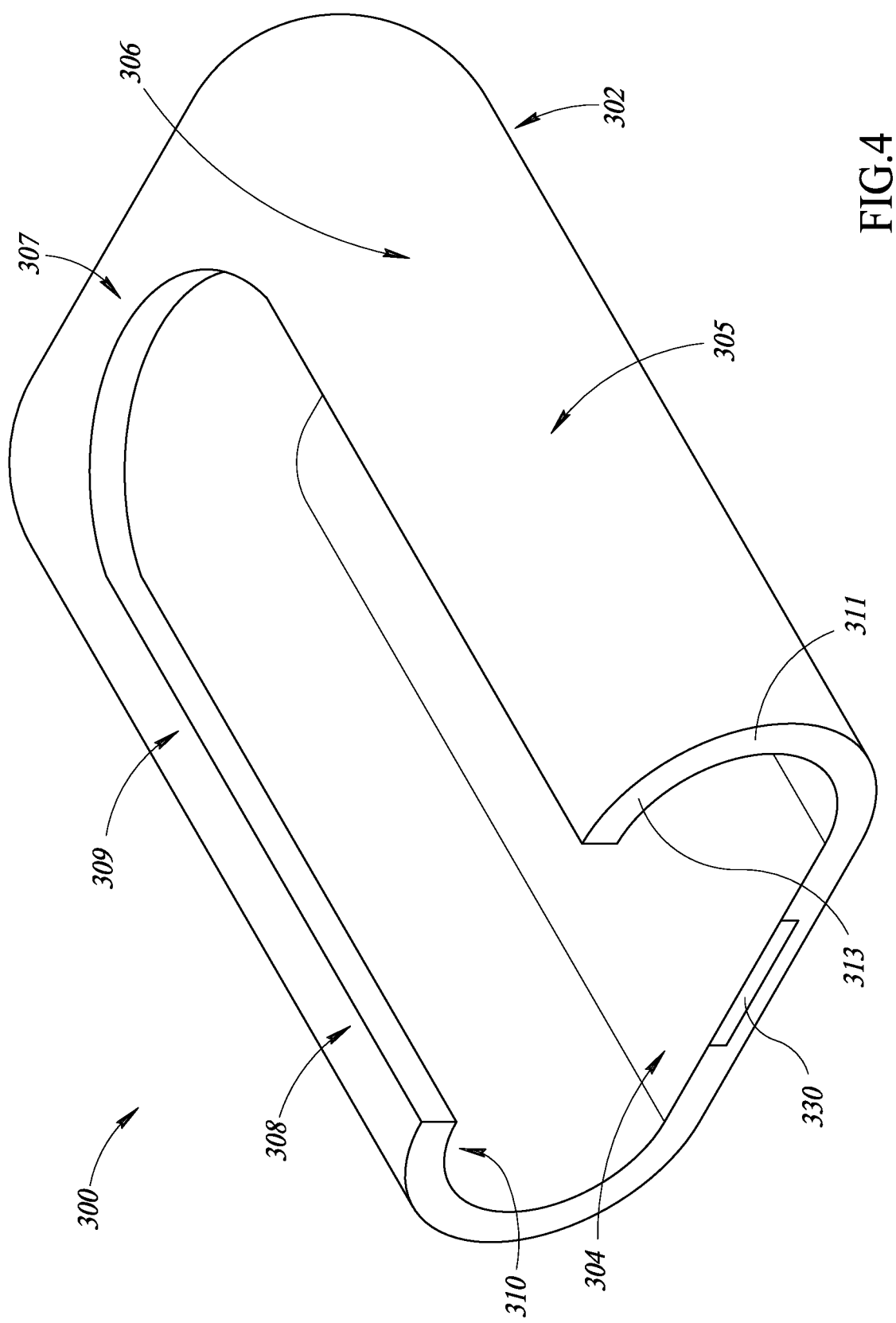
FIG. 4 is a isometric view of an enclosed charging pad according to one embodiment of the present disclosure.

Referring to FIG. 4, an embodiment of an enclosed charging pad 300 is depicted. The enclosed charging pad 300 may have all of the features of the charging pad 200 discussed above. In addition to those features, the charging pad 300 may include means for shielding ultraviolet light and aiding in reducing the amount of ultraviolet light that escapes from the shielded charging pad 300.

The housing 302 of the shielded charging pad 300 may include a base 304 with a power port 330 and one or more sidewalls 305, 307, 309. The sidewalls 305, 309 extend from opposing sides of the base 304 of the shielded charging pad 300. In some embodiments of the charging pad 300, the sidewalls 305, 309 extend outward from the base 304 and curve upward to form a side portion, for example side portion 311 of sidewall 305. The sidewalls 305, 309 may continue to curve upward and inward to form a top or roof portion, for example the roof portion 308 of sidewall 309 and the roof portion 313 of sidewall 305. The roof portion 308 may extend over only a portion of the base 304, as shown in FIG. 4, or the roof portion 308 may extend over the entire base 304 and, for example, join the first sidewall 305 with the second sidewall 309. In some embodiments, the roof portions 308, 313 may not extend over the base 304 or may be omitted altogether.

The shielded charging pad 300 may also include a third sidewall or end wall, for example, a sidewall 307. The sidewall 307 extends outward from the base 304 and curves upward to form a side portion, and continues to curve upward and inward to form a top or roof portion. As shown in FIG. 4, the sidewall 307 may join with the first and second sidewalls 305, 309 to form a continuous structure including the three sidewalls 305, 307, 309. In some embodiments, the sidewall 307 may not join with the first or second sidewalls 305, 309.

The sidewalls 305, 307, 309 may be opaque to ultraviolet light or may have an outer surface 306 that is opaque to ultraviolet light. The outer surface 306 may be opposite an inner surface 310. The inner surface 310 faces the base 304 of the shielded charging pad 300.

As discussed above with reference to the charging pad 200, the housing 302 of the shielded charging pad 300 may include ultraviolet light emitters. The ultraviolet light emitters may be located within the base 304 and oriented to emit ultraviolet light upward out of the base and towards an item, such as a remote control 100 that may be positioned on the base 304. Ultraviolet light emitted from the base 304 of the shielded charging pad 300 may have a limited disinfecting capabilities with respect to some surfaces of the remote control 100 because the ultraviolet light emitted from the base 304 may strike the surfaces of the remote control 100 facing the base, such as the bottom portion 106, but not the other surfaces of the remote control 100, for example the top portion 104 of the remote control 100 facing away from the base 304. To more effectively disinfect the remote control 100, ultraviolet light emitters may be positioned in the sidewalls 305, 307, 309 and the roof portion 308 such that they emit ultraviolet light that may disinfect the sides and top portion 104 of the remote control 100.

Figure 5:
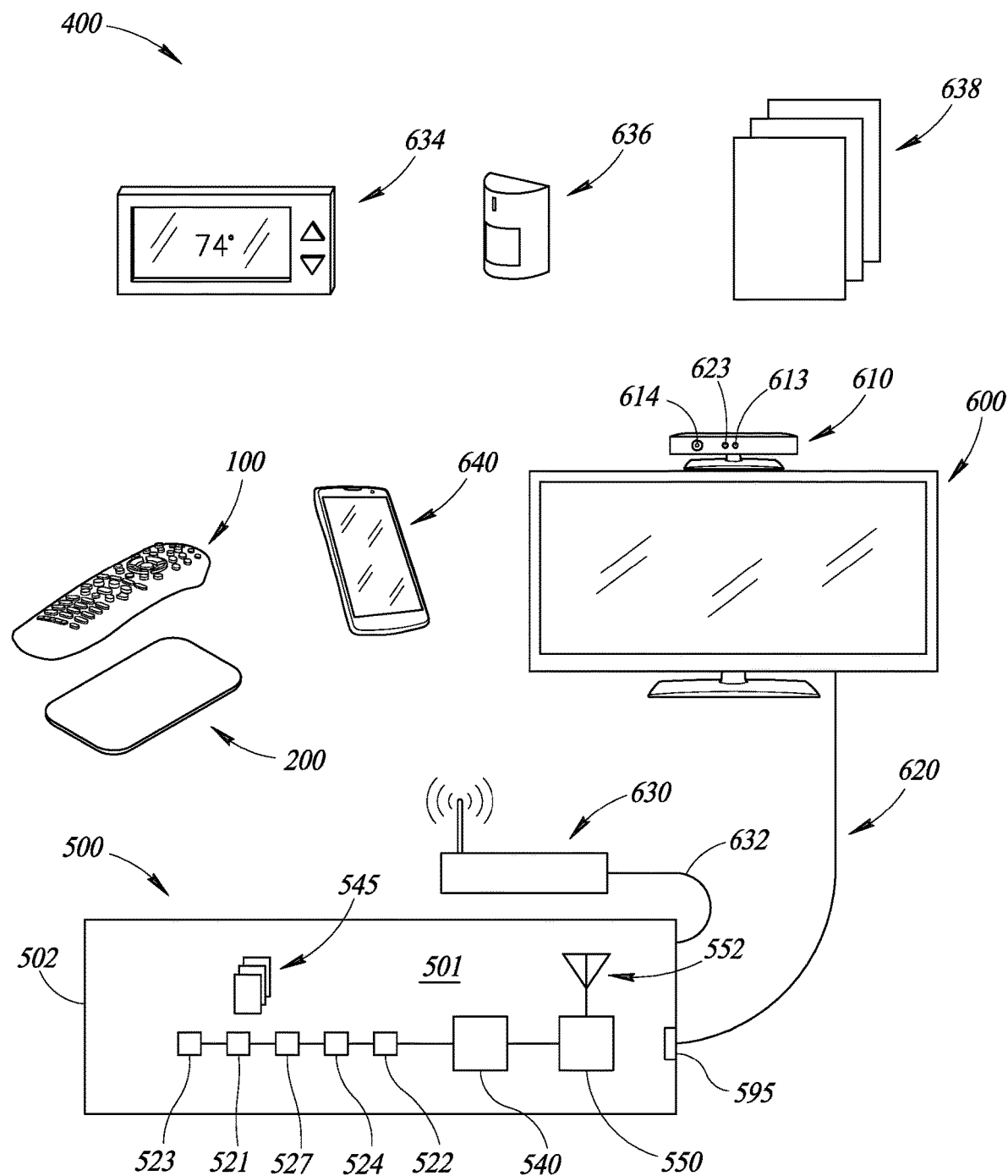
FIG. 5 is a diagram of a system for disinfecting a remote control according to one embodiment of the present disclosure.

FIG. 5 discloses a system 400 for disinfecting a remote control 100. The system 400 includes a set-top box 500 with a housing 502 surrounding an inner cavity 501. The set-top box 500 includes sensors 522, 524 coupled to a controller 540. The light sensor 522 may have a structure and functionality similar to the light sensor 122 discussed above with reference to the remote control 100 in FIG. 1, for example the light sensor 522 may be located beneath a window, not shown, in the housing 502 of the set-top box 500. Likewise, the microphone 524, the controller 540, and the wireless system, including wireless transceiver 550 and antenna 552, may also have a similar structure and functionality as the systems and parts discussed above with respect to the remote control in FIG. 1.

The set-top box 500 may also include a camera 523. The camera 523 may be positioned in or on the set-top box 500 and oriented such that it points towards the space near the set-top box 500, for example, the camera 523 may be oriented such that is has a view of the room in which the camera 523 is placed and, for example, a view of a couch in the room. The camera 523 can be either wired or wirelessly coupled to the controller 540. The camera 523 can transmit information related to the environment near the camera 523. For example, the camera 523 can transmit images to the controller 540 with so-called machine vision capabilities to determine whether people are present in the images.

The set-top box 500 may also include a motion detector 521. Unlike the motion sensors 128, 129 that sense the movements of the remote control 100 in which they are mounted, the motion detector 521 detects movements of people or objects within the field of view of the motion detector 521, through for example, detecting changes in the level of inferred light, measurement of Doppler shifts in emitted microwave or ultrasonic waves, or other methods. The motion detector 521 may be similar to the motion detectors found in motion activated lights or motion detectors in home or office security systems.

The motion detector 521 can be either wired or wirelessly coupled to the controller 540. The controller 540 receives information from the motion detector 521 and may use that information in determining whether a person is near the remote control 100 or set-top box 500. For example, the controller 540 may determine that a person is near the set-top box 500 based on receiving motion information from the motion detector 521 that indicates current movement in the room. The controller 540 may determine that a person is not in the room based on receiving information from the motion detector 521 that indicates that no movement has occurred in the room over a period of time, such as 30 or 60 minutes.

The set-top box 500 may also include a clock 527 that keeps track of the date and time. The controller 540 may use the date and time from the clock 527 to aid in determining whether a person is near the remote control 100 or charging pad 200. For example, a person is more likely to be asleep in a bedroom at 3:00 AM than in the living room watching television; therefore, it is likely to be safer to activate ultraviolet emitters to disinfect a remote control 100 that is in a living room at 3:00 AM than to activate ultraviolet emitters to disinfect a remote control 100 in a bedroom at 3:00 AM.

The set-top box 500 may also include a media port, such as an HDMI port 595, connected to a television 600. An HDMI cable 620 transmits messages and information between the television 600 and the set-top box 500. The information transmitted between the television 600 and the set-top box 500 can include a power signal from the television 600 informing the set-top box that the television 600 is turned on. The set-top box 500 and the controller 540 may use this information to aid in determining whether a person is near the remote control 100 or charging pad 200.

The set-top box 500 may also store information 545 related to the viewing habits of the people that use the remote control 100. The set-top box 500 may monitor viewing habits of people who use the television, the network traffic near the set-top box 500 or remote control 100, information from the motion detector 521, and other activities and may use that information to predict when it may be appropriate to activate ultraviolet emitters to disinfect the remote control 100.

Many people in the household can use the remote control 100 and therefore, to help prevent the spread of containments from one person to another, the system 400 may determine when the remote control 100 is likely to change users. For example, a child might typically use the remote control 100 in the morning and afternoon while an adult is likely to use the remote control 100 in the late evening. The system 400 may make determination with respect to who is using or likely to use the remote control 100 based on the content of the media watched on the television, e.g., cartoons and teen programing in the morning and afternoon, before 8:00 PM and crime dramas in the evening, after 9:00 PM. The remote control 100 may also observe that the remote control 100 is rarely used between 8:00 PM and 8:20 PM, which may coincide with putting the child to bed.

If the remote control 100 observes such behavior, it may proactively activate the ultraviolet emitters to disinfect the remote control 100 after the remote control 100 is still for a relatively short period of time, for example, after five minutes. On the other hand, if the system 400 determines that a user nearly always watches a particular television show between 8:00 PM and 9:00 PM on Wednesday nights, but not the other nights of the week, the system may not activate the ultraviolet emitters after only five minutes of inactivity on Wednesday nights between 8:00 PM and 9:00 PM because it is likely the user may walk into the room to begin watching the particular television show.

The system 400 may use other devices and systems to aid in determining when people are not present in the room with the remote control 100 and when to activate the ultraviolet emitters.

The system 400 may include a thermostat 634. The thermostat 634 may be connected to a network or the internet through, for example, a wireless access point 630. The thermostat 634 may include smart features such as motion sensors and other devices and logic to determine when a user is present and when they are away. The thermostat 634 may also include temperature set points to control the temperature based on the time and day. The system 400 may use the temperature set point, motion, and other information to determine when a person is likely not near the remote control 100 and when to activate the ultraviolet emitters.

The system 400 may include a phone 640. The phone 640 may be connected to a network or the internet through, for example, a wireless access point 630. The phone 640 may also include Bluetooth or Wi-Fi direct communication capabilities that may act as proximity detectors. For example, the wireless transceiver 550 in the set-top box 500 may also include Bluetooth or Wi-Fi direct communication capabilities so that when the phone 640 is within range of wireless transceiver 550 the system 400 may detect such proximity and determine that a person is located near the remote control 100 or charging pad 200 and to not activate the ultraviolet emitters. Additionally, the phone 640 may include a GPS receiver or other means of determining the phone's 640 location. The phone 640 may communicate its location, based on information from the GPS receiver, to the system 400 for use in determining when to activate the ultraviolet emitters.

The system 400 may include an alarm system 636. The alarm system 636 may include a motion detector, electronic door locks, a key pad for user input, and other devices a person of skill in the art would understand as associated with an alarm system. The alarm system 636 may also be connected in electronic communication with the system 400 and the set-top box 500, in particular. The system can use information from the alarm system 636 to determine whether a person is near ultraviolet emitters. For example, motion sensors placed in various rooms in the house can tell the system 400 which rooms in the house contain people, the electronic door locks can inform that a person has arrived at the house, and the keypad can inform the system 400 when the alarm system is activated in an away mode or sleep mode.

The system 400 may also include a game console 610 which may also include an IR emitter 614, an IR receiver 613, and a camera 623. The camera 623 may have functionality similar to that of the camera 523 associated with the set-top box 500. The IR emitter 614 and IR receiver 613 can function as motion detectors and, in more sophisticated embodiments, track the movement of people within the field of view of the IR emitter 614 and IR receiver 613. The game console 610 can send this information to other devices in the system 400 that can use the information to determine whether a person is near and when to activate the ultraviolet emitters.

Cameras, such as the camera 523 associated with the set-top box 500, or the camera 623 associated with the game console can also detect the presence of specific people, for example through facial recognition or by the shape or other attributes of the body. The system 400 may store user profiles as part of the information 545 stored on the set-top box. The profiles may include the viewing habits and location habits of the various users of the remote control 100 and may be used to predict the time during which a person is likely to be away from the remote control 100.

In addition to using a video camera to detect who is present, the system 400 may also detect the presence of particular people based on voice recognition using a microphone or detection of particular mobile devices associated with particular people, such as a user's smartphone 640 or other devices. The system may update or load user profiles based on the presence or absence of a particular person at particular times.

The system 400 may also include a wireless access point 630. The wireless access point 630 can connect the components, such as the devices and sensors that are associated with the system 400, together and facilitate the transfer of information between the components. The system 400 may also include a wired network 632 that can connect the devices and sensors together.

In addition to connecting the components of the system 400 together, the access point 630 and wired network 632 may act as sensors for the system. For example, they can send information regarding the devices connected to the network and the traffic on the network to the set-top box 500 or remote control 100. The system 400 can use the network information to aid in determining whether a person is near the remote control 100, the charging pad 200, or the ultraviolet emitters.

The system 400 may also include other connected devices 638. A person of skill in the art would understand that the system 400 can use any of a myriad of other devices to determine the presence of a person and whether to activate the ultraviolet emitters. For example, key fobs for cars can include proximity sensors, watches and phones may include near field communication capabilities, activity trackers may communicate over wireless networks, and sensors and locks on doors, vehicle tracking and location systems, and other devices can monitor and report on the location of people and objects that the system 400 can use to determine the presence of a person and whether to activate the ultraviolet emitters.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of determining when to activate an ultraviolet light emitter, the method comprising:
transmitting sound waves from a sonar transmitter;
receiving sound pressure level information from a microphone;
receiving temperature information indicating a temperature;
determining that a current time is during one of: a first time period in which a first threshold temperature is used and a second time period in which a second threshold temperature is used, the first threshold temperature being greater than the second threshold temperature;
in response to determining that the current time is during the first time period, determining whether the temperature indicated by the temperature information is above the first threshold temperature and determining whether a sound level indicated by the sound pressure level information is below a threshold sound level;
in response to determining that the temperature indicated by the temperature information is above the first threshold temperature and determining that the sound level indicated by the sound pressure level information is below the threshold sound level, determining that the location of the person is not near the ultraviolet light emitter;
in response to determining that the current time is during the second time period, determining whether the temperature indicated by the temperature information is above the second threshold temperature and determining whether the sound level indicated by the sound pressure level information is below the threshold sound level;
in response to determining that the temperature indicated by the temperature information is above the second threshold temperature and determining that the sound level indicated by the sound pressure level information is below the threshold sound level, determining that the location of the person is not near the ultraviolet light emitter; and
in response to determining that the location of the person is not near the ultraviolet light emitter, activating the ultraviolet light emitter.

2. The method of claim 1, wherein:
the determining whether the sound level indicated by the sound pressure level information is below the threshold sound level includes determining that a sound pressure level detected by the microphone that is greater than a threshold sound pressure level has not been detected by the microphone during a predetermined period of time.

3. The method of claim 1, wherein:
the transmitting sound waves from the sonar transmitter includes transmitting sound waves from a plurality of sonar transmitters.

4. The method of claim 1, further comprising:
receiving information indicating a learned schedule of at least one person,
wherein the determining whether the information indicates the location of the person is not near the ultraviolet light emitter includes determining whether the information indicates the location of the person is not near the ultraviolet light emitter based on the information indicating the learned schedule of the at least one person.

5. The method of claim 1, further comprising:
positioning the sonar transmitter within an inner cavity of a remote control device;
positioning the microphone within the inner cavity of the remote control device; and
positioning the ultraviolet light emitter within the inner cavity of the remote control device.

6. The method of claim 1, further comprising:
coupling a light pipe to the ultraviolet light emitter; and
directing ultraviolet light from the ultraviolet light emitter to an outer surface of housing via the light pipe.

7. The method of claim 1, further comprising:
providing a light guide that receives ultraviolet light from the ultraviolet light emitter; and
distributing the ultraviolet light along an inner surface of a housing via the light guide.

8. A remote control device, comprising:
an ultraviolet light emitter;
at least one sonar transmitter which, in operation, transmits sound waves;
a microphone; and
a controller which, in operation,
receives sound pressure level information from the microphone,
receives temperature information indicating a temperature;
determines that a current time is during one of: a first time period in which a first threshold temperature is used and a second time period in which a second threshold temperature is used, the first threshold temperature being greater than the second threshold temperature;

in response to determining that the current time is during the first time period, determines whether the temperature indicated by the temperature information is above the first threshold temperature and determines whether a sound level indicated by the sound pressure level information is below a threshold sound level;

in response to determining that the temperature indicated by the temperature information is above the first threshold temperature and determining that the sound level indicated by the sound pressure level information is below the threshold sound level, determines that the location of the person is not near the ultraviolet light emitter and activating the ultraviolet light emitter;

in response to determining that the current time is during the second time period, determines whether the temperature indicated by the temperature information is above the second threshold temperature and determines whether the sound level indicated by the sound pressure level information is below the threshold sound level;

in response to determining that the temperature indicated by the temperature information is above the second threshold temperature and determining that the sound level indicated by the sound pressure level information is below the threshold sound level, determines that the location of the person is not near the ultraviolet light emitter, and in response to determining that the location of the person is not near the ultraviolet light emitter, activates the ultraviolet light emitter.

9. The remote control device of claim 8, wherein:
the controller, in operation, determines whether the sound level indicated by the sound pressure level information is below the threshold sound level by determining that a sound pressure level detected by the microphone that is greater than a threshold sound pressure level has not been detected by the microphone during a predetermined period of time.

10. The remote control device of claim 8, wherein:
the at least one sonar transmitter includes a plurality of sonar transmitters, which, in operation, transmits sound waves.

11. The remote control device of claim 8, further comprising:
a receiver which, in operation, receives information indicating a learned schedule of at least one person,
wherein the controller, in operation, determines whether the information indicates the location of the person is not near the ultraviolet light emitter based on the information indicating the learned schedule of the at least one person.

12. The remote control device of claim 8, further comprising:
an inner cavity in which the sonar transmitter, the microphone, and the ultraviolet light emitter are disposed.

13. The remote control device of claim 8, further comprising:
a housing in which the ultraviolet light emitter is disposed; and a light pipe coupled to the ultraviolet light emitter, wherein the light pipe directs ultraviolet light from the ultraviolet light emitter to an outer surface of the housing.

14. The remote control device of claim 8, further comprising:
a housing in which the ultraviolet light emitter is disposed; and
a light guide that receives ultraviolet light from the ultraviolet light emitter and distributes the ultraviolet light along an inner surface of the housing.

15. A system, comprising:
a remote control device that includes an ultraviolet light emitter; and
a set-top box device that includes at least one sonar transmitter, a microphone, and a controller which, in operation,
receives sound pressure level information from the microphone,
receives temperature information indicating a temperature;
determines that a current time is during one of: a first time period in which a first threshold temperature is used and a second time period in which a second threshold temperature is used, the first threshold temperature being greater than the second threshold temperature;
in response to determining that the current time is during the first time period, determines whether the temperature indicated by the temperature information is above the first threshold temperature and determines whether a sound level indicated by the sound pressure level information is below a threshold sound level;
in response to determining that the temperature indicated by the temperature information is above the first threshold temperature and determining that the sound level indicated by the sound pressure level information is below the threshold sound level, determines that the location of the person is not near the ultraviolet light emitter and activating the ultraviolet light emitter;
in response to determining that the current time is during the second time period, determines whether the temperature indicated by the temperature information is above the second threshold temperature and determines whether the sound level indicated by the sound pressure level information is below the threshold sound level;
in response to determining that the temperature indicated by the temperature information is above the second threshold temperature and determining that the sound level indicated by the sound pressure level information is below the threshold sound level, determines that the location of the person is not near the ultraviolet light emitter of the remote control device, and
in response to determining that the location of the person is not near the ultraviolet light emitter, activates the ultraviolet light emitter of the remote control device.

16. The system of claim 15, wherein:
the controller, in operation, determines whether the sound level indicated by the sound pressure level information is below the threshold sound level by determining that a sound pressure level detected by the microphone that is greater than a threshold sound pressure level has not been detected by the microphone during a predetermined period of time.

17. The system of claim 15, wherein:
the at least one sonar transmitter include a plurality of sonar transmitters, which, in operation, transmits sound waves.

18. The system of claim 15, wherein:
the set-top box device includes a receiver which, in operation, receives information indicating a learned schedule of at least one person,
wherein the controller, in operation, determines whether the information indicates the location of the person is not near the ultraviolet light emitter of the remote control device based on the information indicating the learned schedule of the at least one person.

19. The system of claim 15, wherein the remote control device further comprises:
a housing in which the ultraviolet light emitter is disposed; and
a light pipe coupled to the ultraviolet light emitter, wherein the light pipe directs ultraviolet light from the ultraviolet light emitter to an outer surface of the housing.

20. The system of claim 15, wherein the remote control device further comprises:
a housing in which the ultraviolet light emitter is disposed; and
a light guide that receives ultraviolet light from the ultraviolet light emitter and distributes the ultraviolet light along an inner surface of the housing.

* * * * *